(12) United States Patent
Hsu et al.

(10) Patent No.: US 11,679,263 B2
(45) Date of Patent: Jun. 20, 2023

(54) SYSTEMS AND METHODS FOR IMPROVING HEADACHE PAIN

(71) Applicant: Realeve, LLC, Manalapan, FL (US)

(72) Inventors: William Hsu, Santa Clara, CA (US); Ian Welsford, Concord, CA (US); Mark Van Kerkwyk, Gilroy, CA (US); Vimel Ganesan, Mountain View, CA (US)

(73) Assignee: REALEVE, LLC, Manalapan, FL (US)

( * ) Notice: Subject to any disclaimer, the term of this patent is extended or adjusted under 35 U.S.C. 154(b) by 58 days.

(21) Appl. No.: 16/229,202

(22) Filed: Dec. 21, 2018

(65) Prior Publication Data

US 2019/0201694 A1 Jul. 4, 2019

Related U.S. Application Data

(60) Provisional application No. 62/611,303, filed on Dec. 28, 2017.

(51) Int. Cl.
*A61N 1/36* (2006.01)
*A61B 5/00* (2006.01)
*A61N 1/05* (2006.01)

(52) U.S. Cl.
CPC ........ *A61N 1/36075* (2013.01); *A61B 5/4809* (2013.01); *A61B 5/4836* (2013.01); *A61N 1/0546* (2013.01); *A61N 1/3614* (2017.08); *A61B 2562/0219* (2013.01); *A61B 2562/0247* (2013.01)

(58) Field of Classification Search
CPC .............. A61N 1/0546; A61N 1/36075; A61N 1/3614; A61B 5/4809; A61B 5/4836; A61B 2562/0219; A61B 2562/0247
See application file for complete search history.

(56) References Cited

U.S. PATENT DOCUMENTS

| | | | |
|---|---|---|---|
| 8,494,641 B2* | 7/2013 | Boling | A61N 1/36064 607/46 |
| 8,886,325 B2* | 11/2014 | Boling | A61N 1/0558 607/46 |
| 9,233,246 B2* | 1/2016 | Simon | A61N 1/36021 |
| 10,286,213 B2* | 5/2019 | Fletcher | A61N 1/37264 |
| 2003/0018368 A1* | 1/2003 | Ansarinia | A61N 1/36075 607/46 |
| 2006/0149337 A1* | 7/2006 | John | A61N 1/36064 607/45 |
| 2006/0287677 A1* | 12/2006 | Shalev | A61N 1/0548 607/2 |
| 2007/0142874 A1* | 6/2007 | John | A61N 2/006 607/45 |
| 2008/0140149 A1 | 6/2008 | John et al. | |
| 2008/0167700 A1* | 7/2008 | Shalev | A61N 1/0548 607/116 |
| 2008/0172102 A1* | 7/2008 | Shalev | A61N 1/0548 607/45 |

(Continued)

OTHER PUBLICATIONS

Peterlin, B. Lee, et al. "Interictal, circulating sphingolipids in women with episodic migraine a case-control study." Neurology 85.14 (2015): 1214-1223.

*Primary Examiner* — Christopher A Flory
(74) *Attorney, Agent, or Firm* — Stinson LLP (57) ABSTRACT

Methods and systems for improving headache pain by using feedback mechanisms are provided.

7 Claims, 4 Drawing Sheets

(56) References Cited

U.S. PATENT DOCUMENTS

| | | | | |
|---|---|---|---|---|
| 2009/0131739 A1* | 5/2009 | Shalev | A61N 1/0548 600/13 |
| 2009/0216287 A1* | 8/2009 | Ansarinia | A61N 1/3605 607/3 |
| 2011/0160623 A1* | 6/2011 | Shalev | A61N 1/0548 601/2 |
| 2012/0071811 A1* | 3/2012 | Ansarinia | A61N 1/36075 604/20 |
| 2012/0209286 A1* | 8/2012 | Papay | A61N 1/0558 606/129 |
| 2013/0110195 A1* | 5/2013 | Fletcher | A61N 1/37518 607/46 |
| 2013/0116745 A1* | 5/2013 | Fletcher | A61N 1/3787 607/46 |
| 2013/0190838 A1* | 7/2013 | Caparso | A61N 1/36071 607/46 |
| 2013/0245486 A1* | 9/2013 | Simon | A61B 5/4041 600/546 |
| 2013/0274831 A1* | 10/2013 | Otto | A61N 1/36139 607/62 |
| 2013/0310909 A1* | 11/2013 | Simon | A61N 1/0551 607/115 |
| 2014/0257438 A1* | 9/2014 | Simon | A61N 2/02 607/72 |
| 2014/0276195 A1* | 9/2014 | Papay | A61B 5/4893 600/554 |
| 2014/0324118 A1* | 10/2014 | Simon | A61N 1/0456 607/46 |
| 2014/0330345 A1* | 11/2014 | John | A61N 1/36064 607/59 |
| 2014/0371515 A1* | 12/2014 | John | A61N 2/02 600/13 |
| 2015/0148878 A1* | 5/2015 | Yoo | A61N 1/0556 607/118 |
| 2015/0174406 A1* | 6/2015 | Lamensdorf | A61N 1/0548 607/62 |
| 2016/0287869 A1* | 10/2016 | Errico | A61N 1/0456 |
| 2016/0346542 A1* | 12/2016 | Simon | A61B 5/4836 |
| 2017/0072200 A1* | 3/2017 | Fletcher | A61N 1/0529 |
| 2017/0151433 A1* | 6/2017 | Simon | A61N 2/006 |
| 2017/0182285 A1* | 6/2017 | Tyler | A61B 5/4806 |
| 2018/0184907 A1* | 7/2018 | Tran | A61B 5/7264 |
| 2019/0001139 A1* | 1/2019 | Mishra | A61N 1/37205 |
| 2019/0321633 A1* | 10/2019 | Simon | A61B 5/4041 |

* cited by examiner

Inserting an electrode device sized and dimensioned to deliver a stimulation signal to a dorsal nasal nerve structure, the stimulation signal having stimulation parameters
102

Intra-operatively sensing a physiological parameter associated with headache pain, the physiological parameter being tearing; impedance of tissue surrounding the dorsal nasal nerve structure; an electrically evoked signal; biometric data;or a combination thereof
104

Intra-operatively automatically controlling placement of the electrode device adjacent to the dorsal nasal structure, stimulation parameters delivered by the electrode device to the dorsal nasal structure, or both based on the sensed physiological parameter
106

Delivering a stimulation signal via the electrode device to the dorsal nasal structure to improve the patient's headache pain
108

SYSTEMS AND METHODS FOR IMPROVING HEADACHE PAIN

RELATED APPLICATION

The present application claims priority to U.S. Provisional Application No. 62/611,303 filed on Dec. 28, 2017. The present application relates to PCT Application No. PCT/US17/64655, filed on Dec. 12, 2017, which claims priority to U.S. Provisional Application No. 62/430,076, filed on Dec. 5, 2016. This application also relates to U.S. Application No. 62/611,254, filed on Dec. 28, 2017, (Ref. No. ATI-027234 US PRO entitled: "System, Method, and Apparatus for Neurostimulation." All the above-reference applications are incorporated by reference herein in their entirety.

TECHNICAL FIELD

The present disclosure relates to feedback methods and systems for treating headache pain by stimulating a dorsal nasal nerve structure are provided.

BACKGROUND

Headaches are one of the most common ailments, and afflict millions of individuals. The specific etiology of headaches may be difficult to pinpoint. Known sources of headache pain include trauma and vascular, autoimmune, degenerative, infectious, drug and medication-induced, inflammatory (sarcoid), neoplastic (primary or metastatic), metabolic-endocrine, iatrogenic (such as post-surgical), muscloskelatal and myofascial causes. Even if the condition underlying the headache pain is identified and treated, headache pain may persist.

Diagnosis of headache pain will typically include an identification of one or more categories of headaches. There are a variety of different headaches with different features such as migraine headaches and migraine headaches. Migraine headaches, as defined by the International Headache Society (IHS) Classification, are typically unilateral, throbbing headaches lasting from four to seventy-two hours. Migraines are often accompanied by nausea, vomiting, light sensitivity and/or noise sensitivity. Migraine headaches can be further subdivided and sub-classified into a number of different categories, such as, for example, migraine with aura, migraine without aura, and retinal migraine.

Migraines have traditionally been treated with medications to prevent their recurrence and to alleviate acute pain and associated symptoms, such as nausea and vomiting. Non-invasive modalities of migraine treatment, which may be used alone or in combination, have included: diet modification, which may include the avoidance of known headache triggers (such as certain foods); biofeedback and relaxation techniques as well as other psychological modalities; acupuncture; chiropractic manipulation; and physical therapy. Invasive therapeutic procedures have also been implemented, and have included localized anesthetic blocks as well as neurosurgical interventions, such as nerve and ganglion transections and/or resections. Unfortunately, the effectiveness of each therapeutic modality typically varies widely between individual migraine sufferers, and irrespective of the treatment modality used, the suppression of migraine pain is often short-lived, with the pain recurring at levels which are typically less but sometimes equally or rarely more intense than before treatment.

Cluster headaches are so termed due to their repeated occurrence in groups or clusters. Cluster headaches are characterized by intense, stabbing pain usually starting in the region of an eye or temple and localizing to one side of the face. Autonomic features such as lacrimation, nasal congestion, ptosis, conjunctival injection and pupillary changes are common in cluster headaches.

Because of the typically short duration of cluster headaches, therapies designed to abort the pain of an acute attack must have a quick onset of action. Such therapies have included oxygen inhalation, and injections of medication, such as dihydro ergotamine (DHE), ketorolac, or sumatriptan. Non-invasive therapies used to treat cluster headache pain and prevent their recurrence have included use of medications including ergot derivatives, varapamil, lithium, steroids, and sodium valproate; psychological intervention with biofeedback and relaxation techniques; and acupuncture. Anesthetic agents (such as Lidocaine) have been applied to the sphenopalatine ganglia, either directly, using a syringe, or indirectly, by soaking a long cotton swab in the anesthetic and placing the swab intranasally adjacent to the sphenopalatine ganglia, such that the anesthetic diffuses through the nasal mucosa to affect the SPG. Invasive approaches for the treatment of cluster headaches have included localized anesthetic block, surgical resection, radiofrequency, alcohol/phenol infiltration, radiosurgery and cryotherapy of the sphenopalatine ganglia and the trigeminal nerve and ganglion. The invasive approaches for treating cluster headaches are typically used only in headache sufferers who cannot tolerate the non-invasive methods of treatment, or in whom the cluster headaches are refractory and inadequately controlled with non-invasive methods.

SUMMARY

The present disclosure relates to methods and systems for improving headache pain in a patient suffering therefrom.

In an embodiment, a closed-loop therapy delivery system for improving headache pain in a patient suffering therefrom is provided. The system comprises an electrode device sized and dimensioned to deliver a stimulation signal to a dorsal nasal nerve structure. The system also includes a power source in electrical communication with the electrode device. The system further includes a sensor configured to sense a physiological parameter associated with the headache pain and generate a sensor signal based on the physiological parameter. The physiological parameter is tearing, impedance of tissue surrounding the dorsal nasal nerve structure, an electrically evoked signal, biometric data, or a combination thereof. The system also includes a controller in electrical communication with the electrode device and the sensor. The controller is programmed to generate a drive signal to automatically control placement of the electrode, stimulation parameters delivered by the electrode device, or both based on the sensor signal to improve the patient's headache pain.

In another embodiment, a method for improving headache pain in a patient suffering therefrom comprises inserting in the patient an electrode device sized and dimensioned to deliver a stimulation signal having stimulation parameters to a dorsal nasal nerve structure. The method further comprises sensing a physiological parameter associated with the headache pain. The physiological parameter is tearing, impedance of tissue surrounding the dorsal nasal structure, an electrically evoked signal, biometric data, or a combination thereof. The method also includes automatically controlling placement of the electrode device adjacent to the dorsal nasal structure, stimulation parameters delivered by the electrode device to the dorsal nasal structure, or both based on the sensed physiological parameter. The sensing and controlling steps are performed intra-operatively. The method further includes delivering a stimulation signal via the electrode device to the dorsal nasal structure to improve the patient's headache pain.

In another embodiment, a method for improving headache pain in a patient suffering therefrom is provided. The method comprises inserting in the patient an electrode device sized and dimensioned to deliver a stimulation signal having stimulation parameters to a dorsal nasal nerve structure. The method further comprises sensing a physiological parameter associated with the headache pain. The physiological parameter is tearing, impedance of tissue surrounding the dorsal nasal nerve structure, biometric data, an evoked electrical signal, or a combination thereof. The method further includes automatically controlling stimulation of the dorsal nasal nerve structure by initiating delivery of the stimulation signal, adjusting the stimulation parameters of the stimulation signal, or both based on the sensed physiological parameter to improve the patient's headache pain. The sensing and controlling steps are performed post-operatively. The method further includes delivering a stimulation signal via the electrode device to the dorsal nasal structure to improve the patient's headache pain.

In certain embodiments, methods and systems are provided that determine non-paresthesia stimulation therapies, such as burst and high frequency stimulation signals that do not invoke paresthesias, but that still suppress the patient's pain. The methods and systems determine non-paresthesia therapies based on A-delta and C-fiber sensory action potentials (SAPs) or electrically evoked compound action potentials (ECAPs) sensed from an electrode device implanted adjacent to the dorsal nasal nerve structure. Closed-loop systems and methods are provided that sense the A-delta and C-fiber SAP or ECAP component from the dorsal nasal nerve structure. One or more features of interest (e.g. frequency of SAP or ECAP) from the A-delta and C-fiber SAP component or ECAP component are used as feedback to select settings for therapy parameters that define stimulation signals, such as burst and high frequency stimulation signals, as well as lead implant locations, thereby enabling both energy conservation and stimulation efficacy. The pain signals transmitted within A-delta and C fibers are spontaneously generated action potentials that appear as "spikes" in the electrical signal measured at the electrode device implant location. The more pain felt, the higher the SAP frequency, the ECAP frequency or spike frequency of the A-delta and C-fibers. The methods and systems herein seek to suppress or ameliorate pain related SAPs and ECAPs conveyed by the A-delta fibers and/or C-fibers.

DETAILED DESCRIPTION

The present disclosure relates to systems and methods for improving headache pain in a patient suffering therefrom by stimulating a dorsal nasal nerve structure, including the sphenopalatine ganglion (SPG). Certain embodiments relate to open-loop and closed-loop feedback systems and methods to improve the patient's headache pain.

As used herein with respect to a described element, the terms "a," "an," and "the" include at least one or more of the described element including effective combinations thereof unless otherwise indicated. Further, the terms "or" and "and" refer to "and/or" and effective combinations thereof unless otherwise indicated. A "dorsal nasal nerve structure" includes a SPG, a sphenopalatine nerve (SPN) (also called the "pterygopalatine nerve"), a vidian nerve (VN) (also called "the nerve of the pterygoid canal"), a greater petrosal nerve (GPN), a lesser petrosal nerve, a deep petrosal nerve (DPN), or a branch thereof (e.g., a nasopalatine nerve, a greater palatine nerve, an inferior posterior lateral nasal branch of the greater palatine nerve, a lesser palatine nerve, or a superior maxillary nerve). As used herein, "a stimulation signal" delivered to a dorsal nasal nerve structure refers to the ability of an electric field generated by an electrical contact of an electrode device to be transferred to the dorsal nasal nerve structure to have a neuromodulatory effect on the dorsal nasal nerve structure. In such an instance, an electrode is placed adjacent to the dorsal nasal nerve structure such that a stimulation signal is applied directly to the dorsal nasal nerve structure to directly stimulate the dorsal nasal nerve structure. Such direct application of a stimulation signal is in contrast to placing an electrode to a site distal or proximal to the dorsal nasal nerve structure and that does not innervate the dorsal nasal nerve structure (e.g. the trigeminal nerve, a branch of the trigeminal nerve, a trigeminal ganglion, or the vagus nerve) and applying a stimulation signal directly to such distal or proximal sites that indirectly stimulates the dorsal nasal structure. As used herein, "stimulating," "stimulate" or "stimulation" refers to exciting or inhibiting neural activity. As used herein "activating" a dorsal nasal nerve structure refers to a stimulation pulse or signal causing the dorsal nasal nerve structure to fire an action potential as can be indicated by the presence of a signal on an electrical recording of the dorsal nasal nerve structure or by another physiological observable event. Reference to "improving" a patient's headache pain includes treating, reducing the symptoms of, mitigating, or preventing the headache pain.

Figure 1:
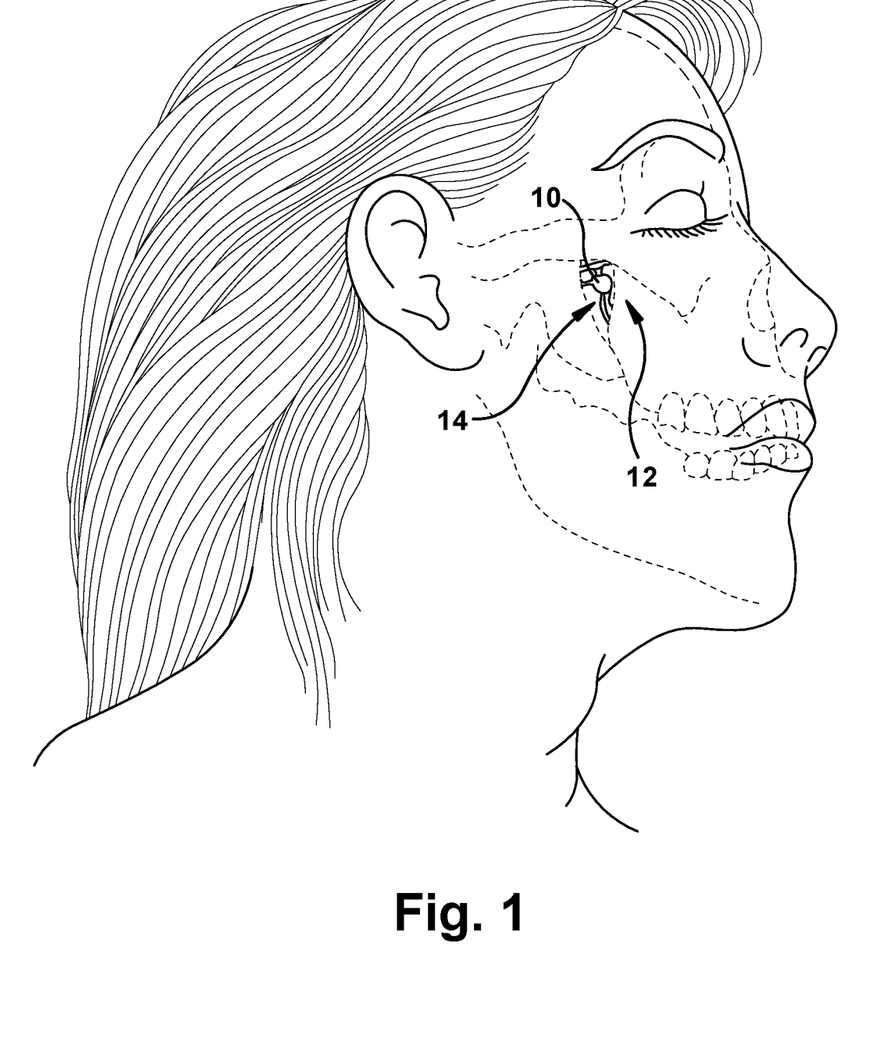
FIG. 1 is a perspective view showing part of the nervous innervation of the anterior craniofacial skeleton.

A brief discussion of the pertinent neurophysiology is provided to assist the reader with understanding certain aspects of the present disclosure. The autonomic nervous system innervates numerous pathways within the human body and consists of two divisions: the sympathetic and the parasympathetic nervous systems. The sympathetic and parasympathetic nervous systems are antagonistic in their action, balancing the other system's effects within the body. The sympathetic nervous system (SNS) usually initiates activity within the body, preparing the body for action, while the parasympathetic nervous system (PNS) primarily counteracts the effects of the SNS. The sphenopalatine ganglia 10 (FIG. 1) are located on both sides of the head. It shall be assumed for the following discussion of the present disclosure that reference is being made to the SPG 10 located on the left side of the head. The SPG 10 is located behind the posterior maxilla 12 in the PPF 14, posterior to the middle nasal turbinate (not shown in detail). The PPF is a small inverted pyramidal space measuring approximately 2 centimeters (cm) high and 1 cm wide and the SPG is approximately 4-5 millimeters (mm) in size. The SPG 10 is part of the parasympathetic division of the autonomic nervous system; however, the SPG has both sympathetic and parasympathetic nerve fibers, as well as sensory and motor nerve fibers either synapsing within the ganglion (e.g., parasympathetic) or fibers that are passing through the ganglion and not synapsing (e.g., sympathetic, sensory and motor). The parasympathetic activity of the SPG 10 is mediated through the greater petrosal nerve (not shown), while the sympathetic activity of the SPG is mediated through the deep petrosal nerve (not shown), which is essentially an extension of the cervical sympathetic chain (not shown). Sensory sensations generated by or transmitted through the SPG 10 include, but are not limited to, sensations to the upper teeth, feelings of foreign bodies in the throat, and persistent itching of the ear. The SPG 10 transmits sensory information, including pain, to the trigeminal system via the maxillary division and ophthalmic division (not shown).

Figure 2:
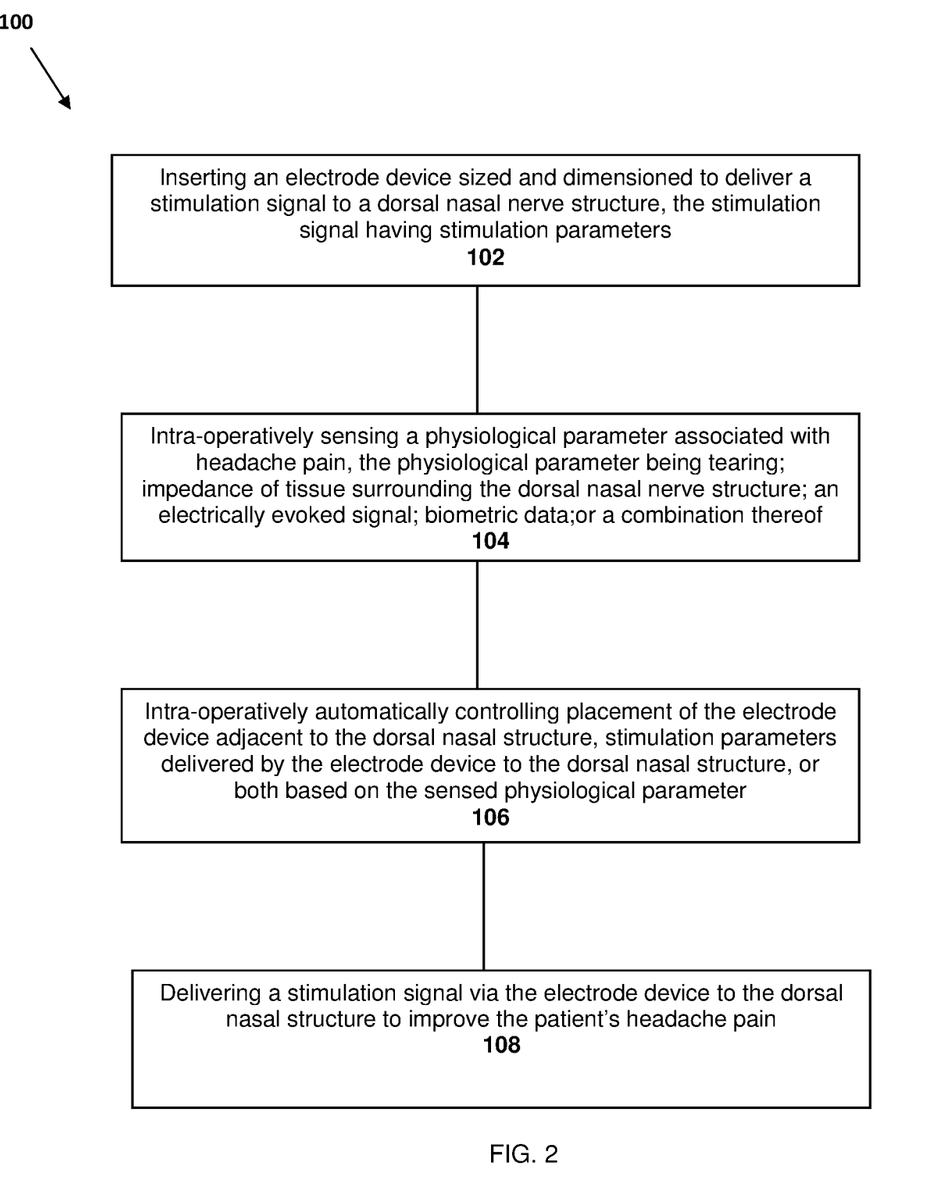
FIG. 2 is a flow chart depicting illustrative steps of a method of improving headache pain in a patient suffering therefrom according to an embodiment of the present disclosure.

Referring to FIG. 2, in an embodiment, a method 100 for improving headache pain in a patient suffering therefrom comprises inserting an electrode device in the patient that is sized and dimensioned to deliver a stimulation signal to a dorsal nasal nerve structure 102. In particular, the electrode device can have electrical contacts that can deliver a stimulation signal having stimulation parameters such as frequency, amplitude, waveform, pulse-width, stimulation pattern such as random versus periodic, location including relative location with respect to other electrical contacts of the electrode device or other stimulation sties, and other stimulation parameters. In certain embodiments, the electrode device is sized and dimensioned for insertion into the PFF. Method 100 further includes intra-operatively sensing a physiological parameter associated with the headache pain 104 and intra-operatively automatically controlling placement of the electrode device adjacent to the dorsal nasal nerve structure, stimulation parameters delivered by the electrode device to the dorsal nasal nerve structure, or both based on the sensed physiological parameter 106. Once the electrode device has been positioned at the ideal location and/or the stimulation parameters have been adjusted to activate the dorsal nasal nerve structure, a stimulation signal can be delivered by the electrode device to the dorsal nasal nerve structure to improve the patient's headache pain 108.

Figure 3:
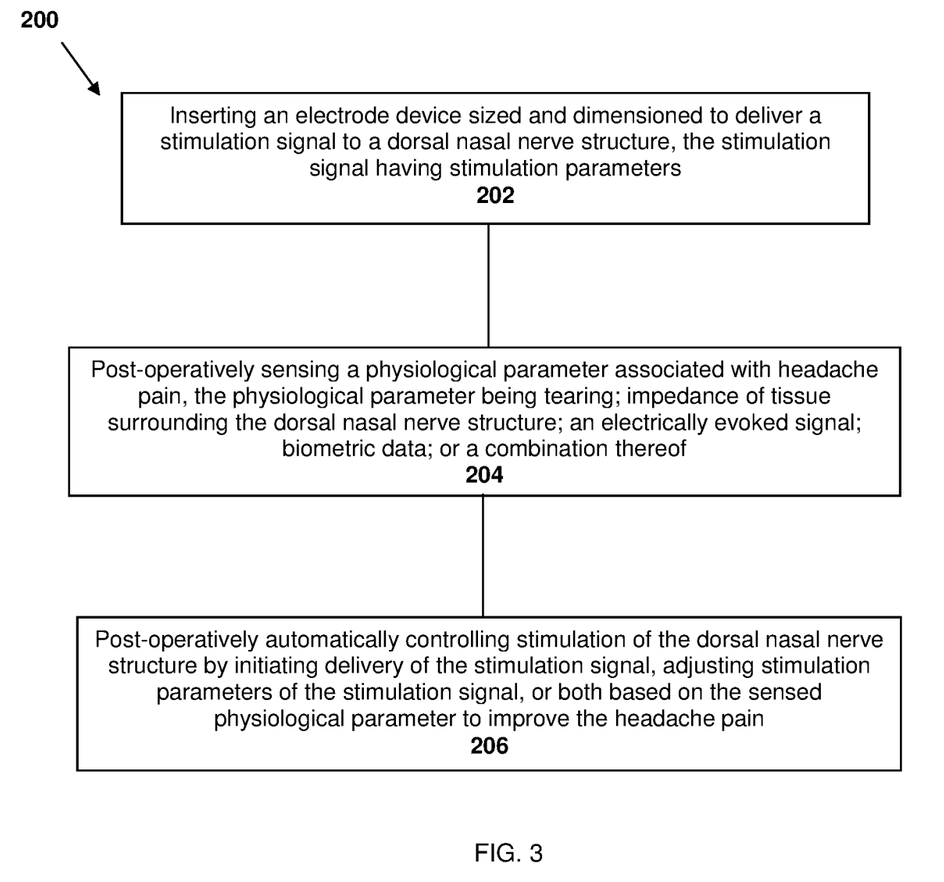
FIG. 3 is a flow chart depicting illustrative steps of a method of improving headache pain in a patient suffering therefrom according to an embodiment of the present disclosure.

Referring to FIG. 3, in another embodiment, a method 200 for improving headache pain in a patient suffering therefrom comprises inserting an electrode device into the patient that is sized and dimensioned to deliver a stimulation signal to a dorsal nasal nerve structure, the stimulation signal having stimulation parameters 202. As with the method steps described above with reference to FIG. 2, the electrode device can have electrical contacts that can deliver a stimulation signal having stimulation parameters such as frequency, amplitude, waveform, pulse-width, stimulation pattern such as random versus periodic, location including relative location with respect to other electrical contacts of the electrode device or other stimulation sites, and other stimulation parameters. In certain embodiments, the electrode device is sized and dimensioned for insertion into the PFF. The method further includes post-operatively sensing a physiological parameter associated with the headache pain 204 and post-operatively automatically controlling stimulation of the dorsal nasal nerve structure by initiating delivery of the stimulation signal by the electrode device, adjusting the stimulation parameters of the stimulation signal by the electrode device, or both based on the sensed physiological parameter to improve the patient's headache pain 206.

Whether the sensing and controlling steps of methods as disclosed herein are performed intra-operatively or post-operatively, the sensed physiological parameter can be, for example, an autonomic response such as tearing; impedance of tissue surrounding the dorsal nasal nerve structure; an electrically evoked signal; or combinations thereof.

With respect to an autonomic response, such as tearing, a plurality of stimulation pulses can be delivered intra-operatively to tissue adjacent to the dorsal nasal nerve structure. Such stimulation pulses can be delivered, for example, by stimulating electrodes on the electrode device or by a delivery tool carrying the electrode device. When at least one of the plurality of stimulation pulses elicits tearing in the patient, this can indicate localization of the dorsal nasal nerve structure and thereby identify the location to implant the electrode device and/or stimulation parameters that are effective in activating the dorsal nasal nerve structure. The placement of the electrode device and/or the stimulation parameters can be automatically controlled in a close-loop fashion by a controller (described in more detail below) when at least one of the plurality of stimulation pulses elicits tearing in the patient. In terms of using tearing as a post-operative sensed physiological parameter, after the electrode device has been implanted, tearing can be sensed to indicate the presence or onset of headache pain. A stimulation signal can be automatically delivered or the stimulation parameters of a stimulation signal can be automatically adjusted to decrease the patient's tearing and to improve the patient's headache pain.

With respect to impedance of tissue surrounding the dorsal nasal nerve structure, an electrode device that is a lead comprising at least two electrical contacts, for example, can be placed in the PPF near the SPG. The rheobase of parasympathetic fibers running through the SPG and associated nerve fibers can correlate with the impedance measured by the lead within the PPF. By measuring the impedance, the overall parasympathetic "tone" of the parasympathetic outflow via the trigeminovascular output pathway, for example, can be determined. When the detected impedance exceeds a pre-determined threshold value for the particular patient (assessed, for example, via trialing or based on a value obtained from a patient population suffering from a similar type of headache pain), the electrode device can be activated to deliver a stimulation signal to the PPF sufficient, for example, to block the cholinergic and peptidergic outflow responsible for cranial autonomic symptoms and improve the patient's headache pain. In terms of intra-operative use of impedance as a sensed physiological parameter, once the impedance of tissue surrounding the dorsal nasal nerve structure exceeds a pre-determined value, the electrode device can be deemed to be in the ideal location to activate the dorsal nasal nerve structure.

With respect to an electrically evoked signal, a plurality of stimulation pulses can be delivered intra-operatively to tissue adjacent to the dorsal nasal nerve structure. The frequency of a SAP signal or an ECAP signal indicating activation of A-delta fibers and C fibers can be detected. The placement of the electrode device and/or the stimulation parameters can be automatically controlled when delivery of at least one of the plurality of stimulation pulses lowers the frequency of the SAP signal, the frequency of the ECAP signal, or the spike frequency of the A-delta and C-fibers below a pre-determined threshold value but still activates the dorsal nasal nerve structure. In terms of using an electrically evoked signal post-operatively, after the electrode device has been implanted, the frequency of SAP or ECAP signals can be detected. If the frequency of the signals exceeds a pre-determined threshold value, the stimulation of the dorsal nasal nerve structure can be automatically controlled by adjusting the stimulation parameters of the stimulation signal to decrease the frequency of the SAP signal, the frequency of the ECAP signal, or spike frequency of the A-delta and C-fibers.

With respect to the physiological parameter being biometric data, such data can include the patient's sleep pattern. A patient's sleep pattern can include data that represents when the time period when the patient is attempting to sleep or is actually sleeping as well as interruptions in the patient's sleep. Such data may be derived from sensors, such as a pressure sensor located in a bed. If the sensor detects pressure commensurate with the presence of the patient, this can indicate that the patient is in bed and is attempting to sleep. If the sensor then detects the lack of commensurate pressure, then this can indicate that the patient is no longer in bed and is not sleeping. Alternatively, the patient can manually indicate to a biometric monitoring device, the beginning and end of a sleep session (such as by pressing a button on a biometric monitoring device to indicate the start and end of a sleep session). A processor can also determine, from data generated by, for instance, the sensor, that a person has engaged in behavior indicative of the start of a sleep session (e.g., by remaining generally motionless for an extended period of time, such as may be detected by accelerometers or other motion sensors). Such motion sensors can also detect interruptions in sleep as indicated by repeated movement of the patient while in bed.

A biometric monitoring device that can be used to collect sleep data can be a wearable biometric monitoring device, such as a wrist-wearable tracker or a handheld device, such as a smart phone. Sensors that sense sleep patterns can be integrated into a mattress pad, mattress, or other component of a bed or bed frame. Such sensors can also be configured to operate from a location remote from a bed such as, for example, a nightstand adjacent to a bed.

The sensed sleep data can include sleep duration, sleep states, sleep stages, sleep state duration, sleep stage durations, interruptions in sleep, waketime, and/or bedtime of the patient. Upon detecting such sleep data, the sensor can generate a sensor signal and the controller can automatically control the initiation of stimulation by the electrode device or adjust the stimulation parameters of the stimulation based on the sensor signal to improve the patient's headache pain. For example, if it is determined that a particular aspect of the patient's sleep, such as sleep duration, affects whether the patient subsequently experiences headache pain, the controller can automatically initiate stimulation of the dorsal nasal nerve structure if the patient's sleep duration is shorter or longer than a pre-determined threshold level for that particular patient.

The biometric data may also include the patient's locomotor activity that can be sensed by an accelerometer or other motion sensor. Upon detecting such locomotor activity, the sensor can generate a sensor signal and the controller can automatically control the initiation of stimulation by the electrode device or adjust the stimulation parameters of the stimulation based on the sensor signal to improve the patient's headache pain. For example, if it is determined that the absence or presence of a certain amount of locomotor activity affects whether the patient subsequently experiences headache pain, the controller can automatically initiate stimulation of the dorsal nasal nerve structure if the patient's locomotor activity is below or above a pre-determined threshold level for that particular patient.

Figure 4:
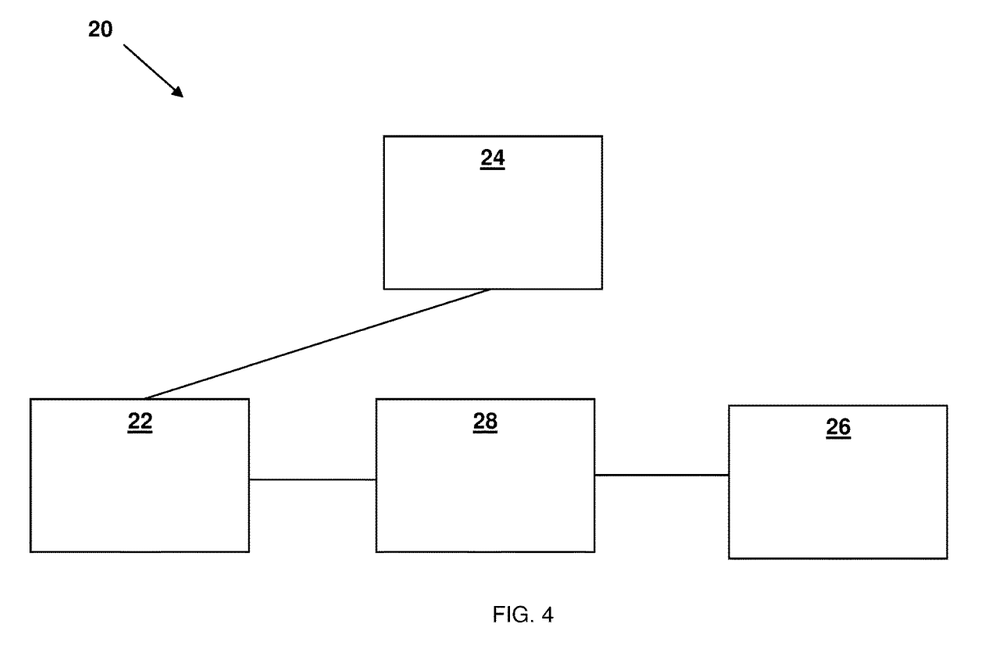
FIG. 4 is a block diagram depicting illustrative components of a neurostimulation system according to an embodiment of the present disclosure.

FIG. 4 is a block diagram of an embodiment of a closed-loop therapy delivery system 20 for improving headache pain in a patient suffering therefrom. System 20 can comprise an electrode device 22 sized and dimensioned to deliver a stimulation signal to a dorsal nasal nerve structure, a power source 24 in electrical communication with electrode device 22, and a sensor 26 configured to sense a physiological parameter associated with the headache pain and generate a sensor signal based on the physiological parameter. The physiological parameter can be tearing; impedance of tissue surrounding the dorsal nasal nerve structure; an electrically evoked signal such as a SAP signal or ECAP signal; biometric data or a combination thereof. System 20 can further include controller 28 in electrical communication with electrode device 22 and sensor 26. Controller 28 can be programmed to generate a drive signal to automatically control placement of the electrode device 22, stimulation parameters delivered by electrode device 22, or both based on the sensor signal to improve the patient's headache pain. Two or more components of system 20 can be in wireless communication with one another. In other instances, two or more components of system 20 can be in wired communication with one another. It will be appreciated that some components of system 20 can be in wireless communication with one another while other components are in wired communication with one another.

In an embodiment, the electrode device 22 can be part of a neurostimulator as described in PCT Application No. PCT/US17/64655, U.S. Provisional Application No. 62/430,076, or U.S. Application No. 62/611,254, filed on Dec. 28, 2017, (Ref. No.: ATI-027234 US PRO) entitled: "System, Method, and Apparatus for Neurostimulation," all of which are incorporated by reference herein in their entirety. In certain embodiments, the electrode device 22 is sized and dimensioned for insertion into the PPF of a patient. The neurostimulator can include the electronic components necessary to perform the various functions for applying stimulation therapy via electrode device 22 and for receiving and transmitting data (e.g. stimulation parameters) and/or power from outside of the body. For example, the electronic components can include, for example, application specific integrated circuits (ASICs) with discrete components such as antennas/coils, capacitors, resistors, etc. for power, transmission distribution and control; custom field programmable gate array (FPGA) chips; a system on a chip (SoC); an integrated circuit (IC) with additional components assembled in a package; or a combination thereof. The neurostimulator can also include a programmable memory for storing at least one set of stimulation and control parameters.

Power source 24 provides electrical power to the components of system 20 that require it. Power source 24 can be any of the following, individually or in combination: wireless power, battery power, and charge banks. When power source 24 includes wireless power, it can be configured to receive power from a remote transducer via wireless power transfer technologies, such as inductive coupling, resonate inductive coupling, capacitive coupling, near-field coupling, mid-field coupling, far-field coupling, microwave power, ultrasonic/acoustic power, and light power. When the power source 24 includes battery power, the batteries can be disposable batteries, such as nickel-cadmium batteries or rechargeable batteries, such as lithium-ion batteries. When power source 24 includes charge banks, the charge banks can include capacitors, inductors, and super-capacitors, which can be used on a standalone basis or in combination with the battery and/or wireless power.

Controller 28 can include software programmed to generate a drive signal to automatically control placement of electrode device 22, stimulation parameters delivered by electrode device 22 and other control parameters. For example, controller 28 can control the pulse waveform, the signal pulse width, the signal pulse frequency, the signal pulse phase, the signal pulse polarity, the signal pulse amplitude, the signal pulse intensity, the signal pulse duration and combinations thereof of an electrical signal delivered by electrode device 22 as well as selection of which of a plurality of electrical contacts of an electrode device are activated to deliver an electrical signal. Controller 28 can include, for example, one or more microprocessors under the control of a suitable software program. The controller 28 can be configured to record and store data indicative of physiological parameters associated with headache pain in a patient. Therefore, controller 28 can generate a drive signal to indicate delivery or adjustment of delivery of a stimulation signal by electrode device 22 when a physiological parameter increases or decreases above a certain threshold value (or range of values), such as a normal or baseline level, as described in more detail below.

Sensor 26 senses a physiological parameter associated with headache pain. The sensor can be a sensor, such as a sensing electrode, that is located on the electrode device or can be a separate and distinct sensor. For example, during intra-operative sensing, the sensor can be located on a delivery tool configured to insert the electrode device into the PPF or otherwise in the vicinity of the dorsal nasal nerve structure. Depending on the physiological parameter sensed, the sensor could also be located at an anatomical site distal to the dorsal nasal nerve structure.

With respect to sensing an autonomic response, such as tearing, the sensor can be a moisture sensor. The moisture sensor can be incorporated into an ocular device, such as, for example, contact lenses, a tear duct plug, or eyeglasses. In an intra-operative context, a plurality of stimulation pulses can be delivered to tissue adjacent to the dorsal nasal nerve structure. The plurality of stimulation pulses can be applied by the electrode device or another stimulating electrode to the tissue adjacent to the dorsal nasal nerve structure, such as a stimulating electrode located on a delivery tool. The moisture sensor can detect the occurrence of tearing in the patient and send a sensor signal to the controller indicating localization of the target nasal nerve structure once tearing occurrence has been detected. The controller can generate a drive signal to automatically deploy the electrode device at the location adjacent to the localized dorsal nasal nerve structure. In a post-operative context, the moisture sensor can detect the occurrence of tearing in a patient and send a sensor signal to the controller indicating the onset or presence of headache pain. The controller can generate a drive signal to initiate delivery of a stimulation signal or adjust stimulation parameters of a stimulation signal applied by the electrode device to improve the patient's pain.

With respect to sensing impedance of tissue surrounding the dorsal nasal nerve structure, the sensor can sense impedance of tissue in the vicinity of the implanted electrode device. In an intra-operative context, the sensor can send a sensor signal to the controller indicating the sensed impedance values. The controller can generate a drive signal to automatically deploy the electrode device at the location where the impedance exceeds a pre-determined threshold value. In a post-operative context, once the impedance value exceeds the pre-determined threshold value, the controller can generate a drive signal to initiate delivery of a stimulation signal or adjust stimulation parameters of a stimulation signal applied by the electrode device to improve the patient's headache's pain.

With respect to an electrically evoked signal, the sensor can be a sensing electrode that measures SAP signals or ECAP signals elicited from stimulation pulses applied by the electrode device or another stimulating electrode to the tissue adjacent to the dorsal nasal nerve structure, such as a stimulating electrode located on a delivery tool. In an intra-operative context, the sensor can detect the frequency of the SAP signals, the ECAP signals or the spike frequency of A delta and C fibers. The controller can generate a drive signal to automatically deploy the electrode device at the location where the frequency of the SAP signals, the ECAP signals or the spike frequency of the A delta or C fibers is below a pre-determined threshold value but still activates the dorsal nasal nerve structure. In a post-operative context, once the frequency of the SAP signal, the ECAP signal, of the spike frequency of the A delta or C fibers exceeds a pre-determined threshold value, the controller can generate a drive signal to initiate delivery of a stimulation signal or adjust stimulation parameters of a stimulation signal applied by the electrode device decrease the frequency of SAP signal, the ECAP signals or the spike frequency of the A delta or C fibers to improve the patient's headache's pain.

With respect to sensing biometric data such as sleep, the sensor can be a pressure sensor or a motion sensor located on or near the patient's bed and the sensor can send a sensor signal to the controller indicating sensed sleep data. The controller can generate a drive signal to automatically initiate delivery of a stimulation signal or adjust stimulation parameters of a stimulation signal applied by the electrode device based on the sensor signal from the sleep sensor to improve the patient's headache's pain. If the biometric data is locomotor activity, the sensor can be a motion sensor located on the electrode device or an implantable part of a neurostimulator in electrical communication with the electrode device. The controller can generate a drive signal to automatically initiate delivery of a stimulation signal or adjust stimulation parameters of a stimulation signal applied by the electrode device based on the sensor signal from the motion sensor to improve the patient's headache's pain.

Another embodiment provides electrode devices, systems, and method of using the same for treating headache pain that generates stimulation signals that produce paresthesia (also referred to herein as paresthesia signals) and also stimulation signals that do not produce paresthesia in patients (also referred to herein as non-paresthesia stimulation signals). Such systems allow a practitioner to control the stimulation therapy so that it can either produce paresthesia or not produce paresthesia by varying the stimulation parameters of the stimulation signals. Stimulation parameters that can affect whether a stimulation signal generates paresthesia include, for example, frequency, amplitude, pulse width, stimulation pattern (such as, for example, random vs. periodic), location of the electrical contacts of the electrode device, and relative location of the electrode contacts if more than one dorsal nasal nerve structure is stimulated. In certain embodiments, stimulation signals that generate paresthesia (e.g. low frequency stimulation) are delivered during insertion of the electrode device so that the patient can provide feedback regarding such paresthesia to assist the clinician in determining the location to implant the electrode device.

Post-implant, the parameters of the stimulation signal can be adjusted to produce a non-paresthesia stimulation signal (e.g. high frequency stimulation such as, for example, between about 1 kHz to 10 kHz) while still being effective to improve the patient's headache pain. Using SAP analysis, the non-paresthesia stimulation signal can be adjusted to minimize energy consumption while achieving headache control and maintaining patient comfort. For example, of particular interest is the frequency of the SAP that is indicative of A delta and C fiber SAP components, which are used to carry pain signals. The pain signals transmitted within A delta and C fibers appear as "spikes" in the electrical signal measured, for example, at the location of the electrode device. The more pain felt, the higher the SAP frequency or spike frequency of the A delta and C fibers. By monitoring the frequency content of the SAP signal, the stimulation parameters of the non-paresthesia stimulation signal can be titrated/adjusted to minimize pain felt by the patient.

ECAP signals can also be used to adjust non-paresthesia stimulation signals. In such embodiments, the ECAP signal can be sensed and then converted to a frequency domain showing frequency data indicative of activity by A beta, A delta and/or C fibers. The stimulation parameters can be adjusted to control the relative amount of the fibers being stimulated to minimize paresthesia and pain felt by the patient.

Headache pain can result from migraine headaches, including migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; reflex sympathetic dystrophy, cervicalgia (which may be due to various causes, including, but not limited to, muscular, discogenic, or degenerative, including arthritic, posturally related, or metastatic); glossodynia, carotidynia; cricoidynia; otalgia due to middle ear lesion; gastric pain; sciatica; maxillary neuralgia; laryngeal pain, myalgia of neck muscles; trigeminal neuralgia (sometimes also termed tic douloureux); post-lumbar puncture headache; low cerebro-spinal fluid pressure headache; temporomandibular joint disorder; atypical facial pain; ciliary neuralgia; paratrigeminal neuralgia (sometimes also termed Raeder's syndrome); petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia (sometimes also termed lower-half headache, lower facial neuralgia syndrome, Sluder's neuralgia, and Sluder's syndrome); carotidynia; Vidian neuralgia; and causalgia; or a combination of the above.

Each of the disclosed aspects and embodiments of the present disclosure may be considered individually or in combination with other aspects, embodiments, and variations of the disclosure. Unless otherwise specified, none of the steps of the methods of the present disclosure are confined to any particular order of performance.

The invention claimed is:

1. A closed-loop therapy delivery system for improving headache pain in a patient suffering therefrom comprising:
   an electrode device sized and dimensioned to deliver a stimulation signal to a dorsal nasal nerve structure;
   a delivery tool configured to insert the electrode device adjacent the dorsal nasal nerve structure;
   a power source in electrical communication with the electrode device;
   a sensor configured to sense a physiological parameter associated with the headache pain and generate a sensor signal based on the physiological parameter, the physiological parameter being tearing; impedance of tissue surrounding the dorsal nasal nerve structure; an electrically evoked signal; biometric data; or a combination thereof; and
   a controller in electrical communication with the electrode device, the delivery tool, and the sensor, the controller programmed to generate a drive signal to the delivery tool to automatically deploy the electrode adjacent the dorsal nasal nerve structure based on the sensor signal to improve the patient's headache pain.

2. The closed-loop therapy delivery system of claim 1, wherein the physiological parameter is tearing and the sensor is a moisture sensor.

3. The closed-loop therapy system of claim 1, wherein the physiological parameter is impedance of tissue surrounding the dorsal nasal nerve structure.

4. The closed-loop therapy delivery system of claim 1, wherein the physiological parameter is an electrically evoked signal.

5. The closed-loop therapy delivery system of claim 1, wherein the biometric data is sleep of the patient and the sensor is a pressure sensor or a motion sensor.

6. The closed-loop therapy delivery system of claim 1, wherein the biometric data is a locomotor activity of the patient and the sensor is an accelerometer.

7. The closed-loop therapy delivery system of claim 1, wherein the controller is further programmed to determine if the physiological parameter exceeds a pre-determined threshold amount based on the sensor signal, and automatically deploy the electrode adjacent the dorsal nasal nerve structure when the physiological parameter exceeds the threshold amount.

* * * * *